United States Patent [19]
Fayram et al.

[11] Patent Number: 5,601,611
[45] Date of Patent: Feb. 11, 1997

[54] OPTICAL BLOOD FLOW MEASUREMENT APPARATUS AND METHOD AND IMPLANTABLE DEFIBRILLATOR INCORPORATING SAME

[75] Inventors: Timothy A. Fayram, Gilroy; George J. Benedict, Santa Cruz, both of Calif.

[73] Assignee: Ventritex, Inc., Sunnyvale, Calif.

[21] Appl. No.: 286,306

[22] Filed: Aug. 5, 1994

[51] Int. Cl.$^6$ ..................................................... A61N 1/39
[52] U.S. Cl. ................................................. 607/6; 128/692
[58] Field of Search ................................ 607/6, 23, 24; 128/634, 691, 692, 673

[56] References Cited

U.S. PATENT DOCUMENTS

| | | | |
|---|---|---|---|
| 3,136,310 | 6/1964 | Meltzer | 128/634 |
| 3,511,227 | 5/1970 | Johnson | 128/634 |
| 4,166,695 | 9/1979 | Hill et al. | 356/28 |
| 4,202,339 | 5/1980 | Wirtzfeld et al. | 607/22 |
| 4,223,680 | 9/1980 | Jobsis | 128/633 |
| 4,249,540 | 2/1981 | Koyama et al. | 128/666 |
| 4,402,601 | 9/1983 | Riva | 356/28.5 |
| 4,691,709 | 9/1987 | Cohen | 128/692 |
| 4,746,211 | 5/1988 | Ruth et al. | 356/28.5 |
| 4,791,935 | 12/1988 | Baudino et al. | 128/692 |
| 4,796,620 | 1/1989 | Imran | 128/706 |
| 4,860,749 | 8/1989 | Lehmann | 128/419 |
| 4,880,005 | 11/1989 | Pless et al. | 128/419 |
| 5,040,538 | 8/1991 | Mortazavi | 128/633 |
| 5,139,020 | 8/1992 | Koestner et al. | 607/24 |
| 5,176,137 | 1/1993 | Erickson et al. | 128/419 |
| 5,183,040 | 2/1993 | Nappholz et al. | 128/419 |
| 5,184,615 | 2/1993 | Nappholz et al. | 128/419 |
| 5,188,106 | 2/1993 | Nappholz et al. | 128/419 |
| 5,193,550 | 3/1993 | Duffin | 128/697 |
| 5,291,885 | 3/1994 | Taniji et al. | 128/633 |
| 5,291,886 | 3/1994 | Katayama | 128/633 |

*Primary Examiner*—William E. Kamm
*Attorney, Agent, or Firm*—Steven M. Mitchell; Mark J. Meltzer

[57] ABSTRACT

A cardiac blood flow sensor includes a light source and a photodetector within a housing. The light source projects a beam through a fiber optic line having a first end optically connected to the housing and a distal tip positioned within the patient's heart. Light intermittently reflected off the moving blood cells is transmitted back through the optic line to the detector, which generates a varying signal proportional to the reflected light, and thus proportional to the blood flow rate within the heart. The flow sensor may be contained in a common housing with a defibrillator that is implanted in a patient. The sensor may remain inactive until a potentially unhealthy heart beat rate is detected, upon which the light source is activated. The defibrillator may be activated only if the flow sensor has detected a blood flow rate below a predetermined level.

12 Claims, 3 Drawing Sheets

OPTICAL BLOOD FLOW MEASUREMENT APPARATUS AND METHOD AND IMPLANTABLE DEFIBRILLATOR INCORPORATING SAME

FIELD OF THE INVENTION

This invention relates to apparatus and method for measurement of fluid flow, and more particularly to measurement of blood flow.

BACKGROUND AND SUMMARY OF THE INVENTION

The human heart may suffer from two classes of rhythmic disorders or arrhythmias: Bradycardia and tachyarrhythmia. Bradycardia occurs when the heart beats too slowly, and may be treated by a common pacemaker delivering low voltage (about 1 V) pacing pulses. Of concern here is tachyarrhythmia, which involves an abnormally high heart rate between about 100 to 200 beats per minute, but without hemodynamic or blood flow efficiency. Of particular concern is a ventricular tachycardia, in which the ventricles have not completely filled before they contract, thus diminishing the volume of blood pumped. The pumping inefficiency is generally proportional to the heart rate. A severe form of tachyarrythmia is fibrillation, which occurs at heart rates of 180 to 300 beats per minute, and involves erratic, disorganized beating that pumps virtually no blood.

Implantable cardioverters/defibrillators (ICD) or pulse generators are used for antitachycardia pacing to correct rapid heart rates by delivering a rapid sequence of pacing pulses of 1 to 10 volts to break the arrhythmia. ICD devices treat severe tachycardia with cardioversion, by delivering a shock of 100 to 750 volts synchronously with the peak of the heart's R-wave signal as detected by an electrocardiogram (ECG). Heart fibrillation receives similar therapy, but the erratic ECG signal may not provide a clear R-wave peak for synchronization.

Normally, the spacing between successive R-wave peaks is used to determine the heart rate. Extremely high or irregular heart rates clearly require therapy. Moderately elevated heart rates may be of ambiguous origin, either from healthy exercise, or from the disorders discussed above. To distinguish between these causes, treatment techniques have included measurement of blood pressure, oxygen saturation, Doppler ultrasound parameters, and ECG morphology. These techniques have limited accuracy and practicality, particularly outside of a clinical setting.

The present invention avoids the limitations of existing techniques and devices by providing a cardiac blood flow sensor that measures blood flow within the heart. The apparatus includes a light source and a photodetector within an implanted housing. The light source projects a beam through a flexible elongated light conduit having a first end optically connected to the housing and a distal tip positioned within the patient's heart. Light reflected off the moving blood cells is transmitted back through the conduit to the detector, which generates a varying signal proportional to the reflected light, and proportional to the blood flow rate within the heart. The flow rate may then be used to determine whether a tachycardia is physiologic or pathologic in origin.

The flow sensor may be contained in a common housing with a defibrillator that is implanted in a patient. The sensor may remain inactive until a potentially unhealthy heart beat rate is detected, upon which the light source is activated. The defibrillator may be activated only if the flow sensor has detected a blood flow rate below a predetermined level.

DETAILED DESCRIPTION OF A PREFERRED EMBODIMENT

Figure 1:
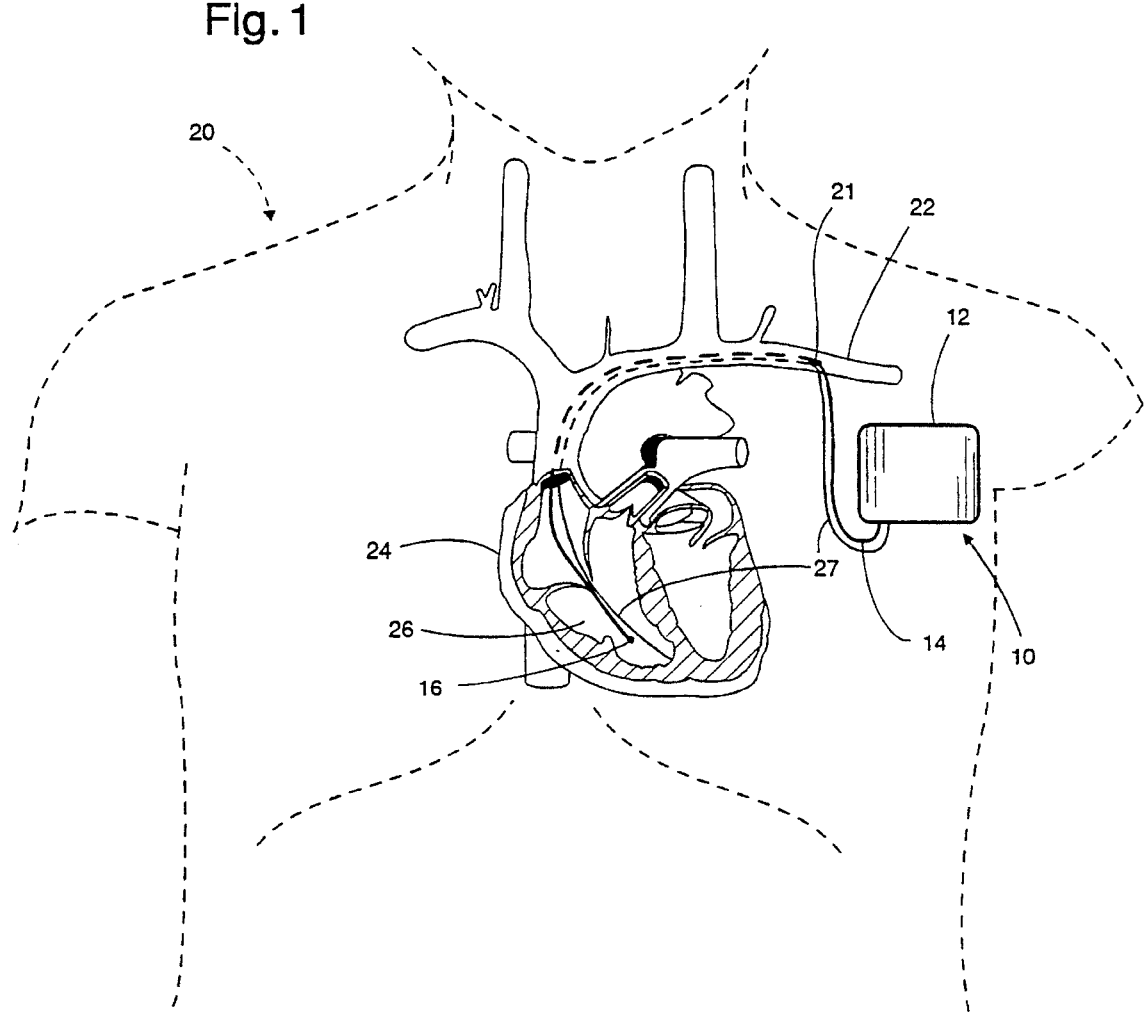
FIG. 1 is an anterior view of a patient implanted with a preferred embodiment of the invention.

FIG. 1 shows an Implantable Cardioverter/Defibrillator (ICD) and flow sensor unit 10, including a single housing 12 and a flexible fiber optic line 14. The optic line serves as a light conduit extending from the housing, and terminates at a distal tip 16. The entire unit 10 is implanted in a patient 20, with the housing 12 located in the patient's pectoral or abdominal region. The optic line 14 extends from the housing to an incision 21 in the patient's subclavian vein 22. The optic line 14 passes through the incision, and extends downwardly through the vein into the heart 24, with the distal tip 16 positioned within the right ventricle 26. The line may be secured to a wall of the right ventricle with the distal tip extending away from the wall. This configuration provides a viewing angle which is more likely perpendicular to the direction of blood flow 25, and may thereby improve the efficiency of the system. A sensing/pacing lead 27 extends from the housing 12 into the ventricle 26, and is secured to the apex of the right ventricle using tines or a screw tip. Surgical implantation may be achieved by encasing the line 14 in a semi-rigid hollow catheter, which may be inserted transvenously. The catheter is removed after the line is positioned.

Figure 2:
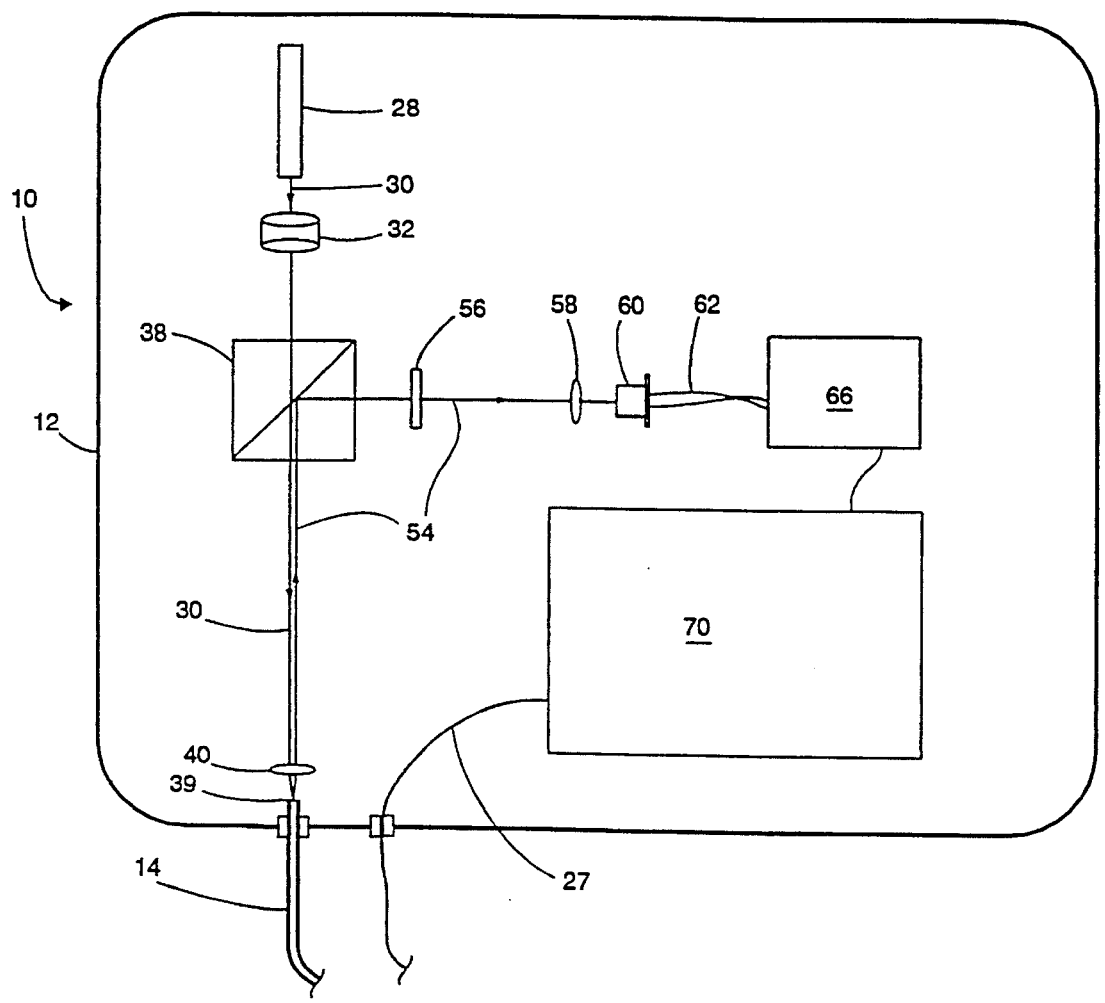
FIG. 2 is a schematic view of the embodiment of FIG. 1.

FIG. 2 shows the ICD and flow sensor unit 10. A laser 28 emits a beam of polarized light along a first beam path 30, through a collimating lens 32 that generates a beam of parallel rays. The beam then passes through a polarization sensitive beam splitter 38, which transmits the polarized and collimated laser beam. The transmitted beam encounters a concentrating lens 40. A first end 39 of the optic line 14 is positioned at the focal point of the lens 40, so that the parallel rays of the beam are focused into the core of the optic line 14. The beam is then transmitted through the line toward the line's distal tip 16.

Figure 3:
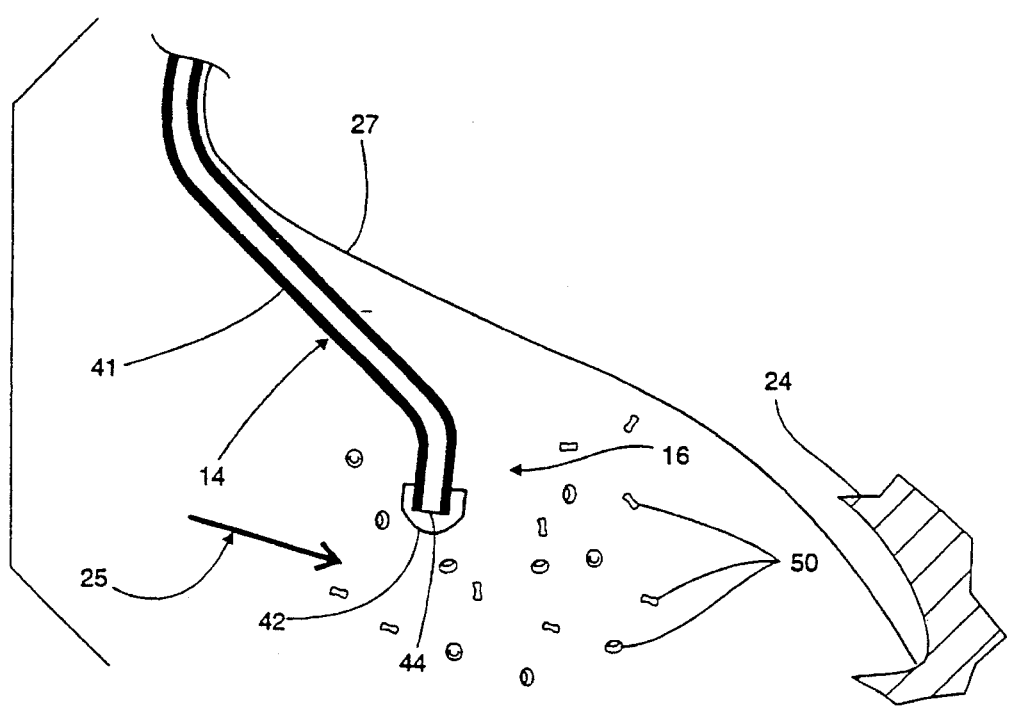
FIG. 3 is an enlarged view of the embodiment of FIG. 1.

FIG. 3 shows the optical details of the distal tip 16 of the optic line 14. The optic line 14 includes a sheath 41 formed of silicone or other biocompatible material to permit long term use in the blood stream. A divergent lens 42 is positioned over the terminus 44 of the line 14 so that light transmitted through the line is intercepted by the lens 42. The lens preferably has a negatively curved surface that diverges the generally parallel rays emitted by the optic line. Alternatively, the lens may have a positive curvature that focuses the generally parallel rays emitted by the optic line to a focal point.

Because the distal tip 16 of the optic line 14 is immersed in blood, the light transmitted through the diverging lens is intermittently reflected off the suspended blood cells 50 passing closely in front of the lens. As a blood cell moves past the diverging lens 42, the amount of reflected light will momentarily increase substantially. With the vast number of cells normally passing by the focal point 48 and generating intermittent reflections, the reflected beam will have a rapidly varying optical signal corresponding to the volume of blood flow. Normal blood flow is estimated to result in a frequency of about 500 kHz, with tachyarrythmia resulting a lower frequency. An absolute blood flow rate is not necessary for a determination of whether to apply therapy; only a determination that the flow rate has undergone a significant relative drop is needed. The frequency threshold for therapy may be set at a level well below the normal frequency as determined for a patient of particular characteristics.

A portion of the reflected light is received by the diverging lens 42, and is transmitted back up the optic line 14 to the housing 12. The light reflected off the hemispherical blood cells will lose its polarization.

Returning to FIG. 2, the intermittent reflected light re-enters the housing 12, and is collimated by lens 40 so that it follows a reflected beam path 54. The reflected beam encounters the beam splitter 38, which reflects 50 percent of the reflected beam perpendicularly from the beam splitter. After leaving the beam splitter, the reflected beam passes through a filter 56 that selectively transmits the wavelength emitted by the laser, reducing optical crosstalk from any stray light of other frequencies. In an alternative embodiment, the filter 56 is omitted. The reflected beam then passes through a lens 58, which focuses the light onto a fast silicon photodetector 60, which generates a varying electrical signal corresponding to the intensity of the intermittent incident light.

The photodetector has an electrical output line 62 that carries the varying signal. A processor 66 is connected to line 62, and processes the varying signal from the photodetector to estimate the blood flow within the ventricle, or to determine if there has been a significant drop in the frequency of the reflected light. The processor is electrically connected to conventional ICD circuitry 70, which provides cardiac therapy by selectably applying a voltage to the connected electrode sensing/pacing lead 27, or to a defibrillation lead electrode(not shown). The lead 27 is capable of sensing the heart rate and providing Brady pacing or anti-tachycardia pacing. An additional return electrode (not shown) providing a "ground" for the high voltage shocks may be placed in the superior vena cava, or may use the housing of a pectorally implanted device. The therapy provided by the defibrillator is not necessarily a defibrillation shock, but is frequently antitachycardia pacing or a cardioversion shock. The defibrillator includes a heart rate sensor (not shown) that permits activation of the flow sensor light source 28 only when the heart rate exceeds a rate that may be problematic. The device may be programmed to provide therapy only if the flow sensor processor 66 indicates a blood flow below the preselected rate.

The processor 66 or ICD circuitry 70 may also be programmed to apply therapy in response to the satisfaction of more complex conditions. A complex function of the heart rate, measured flow rate, characteristics of the patient, and other interacting variables may be used to determine when therapy is indicated.

In the preferred embodiment, the light source may be provided by a solid state laser diode emitting polarized light at a 830 nm or 615 nm wavelength. Alternatives such as light emitting diodes, or other conventional sources may be used. While coherent light is useful for analyzing the motion of extended objects by detecting the reflected pattern variations, and may be usefully employed herein, the illustrated embodiment may use incoherent light to detect microscopic objects that intermittently interrupt the beam. The use of the term light is not intended to limit the invention to visible wavelengths; a wider range of wavelengths may be used.

The distal tip lens 42 is preferably formed of or coated with a material formulated to prevent an accumulation of platelets from obscuring the lens. One suitable coating is Parylene C™, from Specialty Coating Systems of Indianapolis, Ind. A coating thickness of 2 um and coefficient of friction of 0.05 to 0.10 is preferred. The optic line is preferably a single mode 5 to 10 micron type having a diffuse tip, although other types may be employed.

In the secondary embodiment employing a converging lens at the distal tip, a large, non-single mode core fiber optic line having a functional diameter of 0.5–1.0 mm may be used. The light source may be an LED or a laser diode, with a focusing lens being required in conjunction with an LED to concentrate the light onto the fiber. For proper focusing at the distal tip, an air gap should be provided between the end of the optic line and the lens. The focused spot size formed will be on the order of the diameter of the optic line, with a depth of focus approximately twice the optic line diameter. Thus, the spot will encompass numerous blood cells at any one time. Therefore, a lower signal-to-noise ratio is expected with a converging lens than with the preferred diverging lens.

While the invention is described in terms of a preferred embodiment, the claims are not intended to be so limited:

1. An optical blood flow measurement apparatus comprising:
   a housing having a port for transmitting light between the housing interior and exterior;
   a light source within the housing and in optical communication with the port, such that at least a portion of light emitted by the light source is transmitted along a first beam path between the light source and the port;
   a photodetector having an electrical output, the photodetector being responsive to the intensity of light impinging on the detector, the photodetector being positioned within the housing and in optical communication with the port, such that at least a portion of light entering the port from outside the housing is transmitted along a second beam path between the port and the detector to impinge on the detector;
   a processor connected to the photodetector's electrical output for providing a blood flow measurement output; and
   a flexible elongated light conduit having a first end optically connected to the housing port, and a light transmissive distal tip for placement at a site of flowing blood, such that light from the light source is transmitted through the conduit, out of the distal tip, and such that at least a portion of any reflected light is received by the distal tip, and transmitted to the detector to generate a signal;
   whereby light is directed from the light source to the light transmissive tip and into the blood flow and a portion of the light is reflected back to the distal tip and a portion of the reflected light is transmitted to the detector to generate a signal indicative of the blood flow.

2. The apparatus of claim 1 wherein the conduit comprises a fiber optic line.

3. The apparatus of claim 1 wherein at least a portion of the conduit is enclosed by a biocompatible sheath.

4. The apparatus of claim 1 including a lens connected to the distal tip of the conduit.

5. The apparatus of claim 4 wherein the focus lens is a diverging lens.

6. The apparatus of claim 1 including a beam splitter within the housing and within the first and second beam paths, such that portions of the beam paths are coextensive with each other between the beam splitter and the port, and are separate from each other adjacent the respective light source and photodetector.

7. An optical blood flow measurement apparatus comprising:

a housing having a port for transmitting light between the housing interior and exterior;

a light source within the housing and in optical communication with the port, such that at least a portion of light emitted by the light source is transmitted along a first beam path between the light source and the port;

a photodetector having an electrical output the photodetector being responsive to the intensity of light impinging on the detector, the photodetector being positioned within the housing and in optical communication with the port, such that at least a portion of light entering the port from outside the housing is transmitted along a second beam path between the port and the detector to impinge on the detector;

a processor connected to the photodetector's electrical output for providing a blood flow measurement output, wherein the processor includes means for calculating a blood flow rate;

a flexible elongated light conduit having a first end optically connected to the housing port, and a light transmissive distal tip for placement at a site of flowing blood, such that light from the light source is transmitted through the conduit, out of the distal tip, and such that at least a portion of any reflected light is received by the distal tip, and transmitted to the detector to generate a signal;

whereby light is directed from the light source to the light transmissive tip and into the blood flow and a portion of the light is reflected back to the distal tip and a portion of the reflected light is transmitted to the detector to generate a signal indicative of the blood flow.

8. An implantable defibrillator including an optical blood flow measurement apparatus, said measurement apparatus comprising:

a housing having a port for transmitting light between the housing interior and exterior;

a light source within the housing and in optical communication with the port, such that at least a portion of light emitted by the light source is transmitted along a first beam path between the light source and the port;

a photodetector having an electrical output, the photodetector being responsive to the intensity of light impinging on the detector, the photodetector being positioned within the housing and in optical communication with the port, such that at least a portion of light entering the port from outside the housing is transmitted along a second beam path between the port and the detector to impinge on the detector;

a processor connected to the photodetector's electrical output for providing a blood flow measurement output;

a flexible elongated light conduit having a first end optically connected to the housing port, and a light transmissive distal tip for placement at a site of flowing blood, such that light from the light source is transmitted through the conduit, out of the distal tip, and such that at least a portion of any reflected light is received by the distal tip, and transmitted to the detector to generate a signal;

whereby light is directed from the light source to the light transmissive tip and into the blood flow and a portion of the light is reflected back to the distal tip and a portion of the reflected light is transmitted to the detector to generate a signal indicative to the blood flow; and whereby at least a first portion of the defibrillator is contained within the housing and operably connected to the processor, said processor including means to detect a blood flow rate from said reflected light, the defibrillator further including means for detecting a cardiac arrhythmia and means for delivering a therapy in response thereto, the means for detecting a cardiac arrhythmia being responsive to the detected blood flow rate signal from the processor, such that operation of the means for delivering is dependent on the detected blood flow rate.

9. The defibrillator of claim 8 wherein said means for detecting a cardiac arrhythmia includes a heart rate sensor coupled to said processor to provide an indication of said arrhythmia based on a sensed heart rate.

10. A method of measuring blood flow in the blood stream of a patient, the method comprising the steps:

generating light;

transmitting the light through a flexible conduit having a distal tip immersed in the patient's blood stream;

projecting the light from the conduit onto blood cells within the blood stream;

receiving at the distal tip of the conduit reflected light from the cells;

transmitting the reflected light through the conduit to a photodetector;

generating an electrical signal in response to the reflected light intensity;

analyzing the electrical signal to determine the blood flow rate whereby the blood flow rate provides an indication of the hemodynamic performance of the patient's heart.

11. A method of measuring blood flow in the blood stream of a patient, the method comprising the steps:

generating light;

transmitting the light through a flexible conduit having a distal tip immersed in the patient's blood stream;

projecting the light from the conduit onto blood cells within the blood stream and diverging the light within the blood stream such that the light may reflect off blood cells;

receiving at the distal tip of the conduit reflected light from the cells;

transmitting the reflected light through the conduit to a photodetector;

generating an electrical signal in response to the reflected light intensity;

analyzing the electrical signal to determine the blood flow rate whereby the blood flow rate provides an indication of the hemodynamic performance of the patient's heart.

12. The method of claim 10 and further including the step of inserting the distal tip into a chamber of the patient's heart and wherein the step of projecting the light includes projecting the light within the patient's heart.

* * * * *